(12) United States Patent
Lind

(10) Patent No.: US 9,402,675 B2
(45) Date of Patent: Aug. 2, 2016

(54) METHOD AND DEVICES FOR THE TREATMENT OF SKIN LESIONS

(75) Inventor: Zecharia Lind, Clifton, NJ (US)

(73) Assignee: TUVIDERM LLC, Clifton, NJ (US)

( * ) Notice: Subject to any disclaimer, the term of this patent is extended or adjusted under 35 U.S.C. 154(b) by 228 days.

(21) Appl. No.: 13/522,328

(22) PCT Filed: Feb. 3, 2011

(86) PCT No.: PCT/IB2011/050468
§ 371 (c)(1),
(2), (4) Date: Jul. 15, 2012

(87) PCT Pub. No.: WO2011/095941
PCT Pub. Date: Aug. 11, 2011

(65) Prior Publication Data
US 2013/0012932 A1    Jan. 10, 2013

Related U.S. Application Data

(60) Provisional application No. 61/301,709, filed on Feb. 5, 2010, provisional application No. 61/376,537, filed on Aug. 24, 2010.

(51) Int. Cl.
*A61B 18/02* (2006.01)
*A61B 18/00* (2006.01)
*A61B 17/28* (2006.01)

(52) U.S. Cl.
CPC ............. *A61B 18/02* (2013.01); *A61B 18/0218* (2013.01); *A61B 2018/0225* (2013.01)

(58) Field of Classification Search
USPC ....................................... 606/20, 21
See application file for complete search history.

(56) References Cited

U.S. PATENT DOCUMENTS

| 5,516,505 | A | 5/1996 | McDow |
| 6,296,410 | B1 | 10/2001 | Ruizendaal |
| 6,375,652 | B1* | 4/2002 | Griswold ........................ 606/20 |
| 2004/0254607 | A1 | 12/2004 | Wittenberger et al. |
| 2005/0043723 | A1* | 2/2005 | Howlett et al. ................. 606/22 |
| 2006/0167444 | A1* | 7/2006 | Swanson ........................ 606/21 |

* cited by examiner

*Primary Examiner* — Carl H Layno
*Assistant Examiner* — Jon Eric C Morales
(74) *Attorney, Agent, or Firm* — Mark M. Friedman

(57) ABSTRACT

A tweezers device for the application of cryogenic matter directly on a skin lesion while protecting the collateral skin tissue from being damaged by the cryogenic matter, the device comprising an applicator body configured with opposing tweezer arms, each tweezer arm including a cryogenic matter application element such that when the opposing tweezer arms are closed about the skin lesion, the skin lesion is substantially encased by the cryogenic matter application elements.

12 Claims, 17 Drawing Sheets

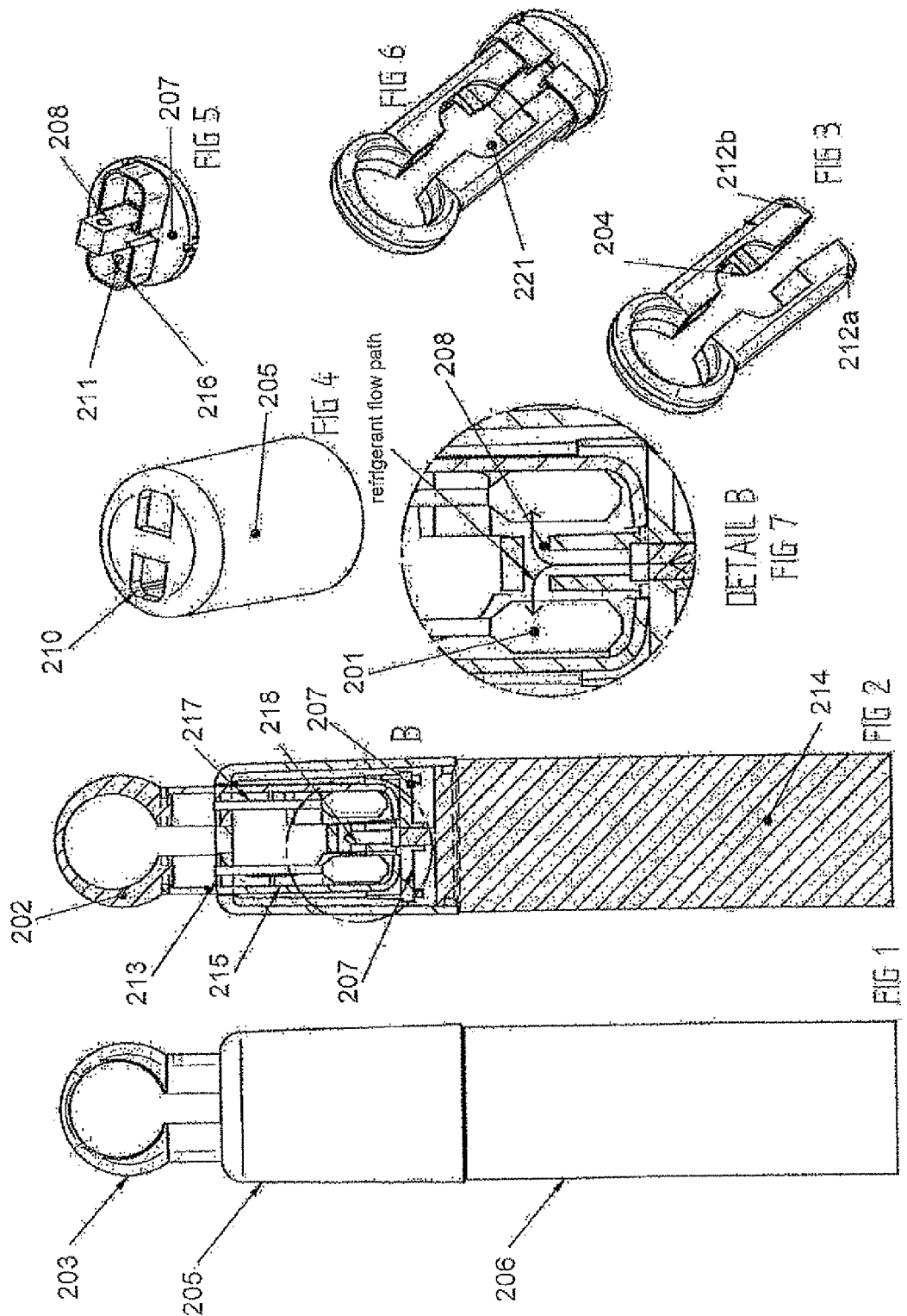

METHOD AND DEVICES FOR THE TREATMENT OF SKIN LESIONS

FIELD AND BACKGROUND OF THE INVENTION

The present invention relates to methods and devices for treating skin lesions and, in particular, it concerns a tweezers type device and method for the application of cryogenic matter directly on a skin lesion while protecting the collateral skin tissue from being damaged by the cryogenic matter.

Skin lesions have typically been treated utilizing several different methods, including surgical methods requiring scalpels, electro-desiccation methods, and various cryogenic methods, including the use of liquid nitrogen. A number of problems are commonly associated with these methodologies, including excessive time requirements, excessive costs, damage to the surrounding tissue, unnecessary pain, requirement for anesthesia, medical complications, and the like.

Electro-desiccation methods typically pose a number of drawbacks such as excessive time requirements and possible hyper-trophic scarring occurring in the patient. These methods should not be used on patients who have pacemakers.

A number of problems may result from the use of scalpels for skin lesion removal, such as the occurrence of hyper-trophic scarring in some patients, the occurrence of bacterial skin infections, bleeding, and excessive time requirements to perform the surgical procedure.

It is known to treat skin lesions commonly referred to as skin tags by the use of cryogenic matter. The use of liquid nitrogen to remove skin lesions poses a number of problems such as the need for expensive storage, unnecessary pain, damage to the adjacent skin, evaporation of the liquid nitrogen material during storage, and possible hypo-pigmentation and hyper-trophic scarring. Another drawback of liquid nitrogen is the high expense of the delivery systems which spray the liquid nitrogen cryogenic material onto the skin and mucous membranes.

The use of cryogenic matter falls into two basic categories. In a first category the cryogenic matter is used to drastically reduce the temperature of the treatment device, such as the device disclosed, in U.S. Pat. No. 6,375,652.

In a second category, the cryogenic matter is applied directly to the lesion itself, such as is disclosed in U.S. Pat. No. 6,296,410 and U.S. Pat. No. 5,516,505. One problem that arises within the second category is damage to collateral skin tissue caused by the cryogenic matter.

There is therefore a need for a device and method for the application of cryogenic matter directly on a skin lesion while protecting the collateral skin tissue from being damaged by the cryogenic matter.

SUMMARY OF THE INVENTION

The present invention is a device and method for the application of cryogenic matter directly on a skin lesion while protecting the collateral skin tissue from being damaged by the cryogenic matter.

According to the teachings of the present invention there is provided, a tweezers device for the application of cryogenic matter directly on a skin lesion while protecting the collateral skin tissue from being damaged by the cryogenic matter, the device comprising an applicator body configured with opposing tweezer arms, each tweezer arm including a cryogenic matter application element such that when said opposing tweezer arms are closed about the skin lesion, the skin lesion is substantially encased by said cryogenic matter application elements.

According to a further teaching of the present invention, There is also provided a canister cap configured for deployment on a canister containing cryogenic matter, the canister cap further configured to insertion of at least that portion of said opposing tweezer arms containing said cryogenic matter application elements such that cryogenic matter released from said canister is applied to said cryogenic matter application elements.

According to a further teaching of the present invention, each of said opposing tweezer arms includes a canister containing cryogenic matter such that cryogenic matter released from each said canister is applied to its corresponding said cryogenic matter application element.

According to a further teaching of the present invention, there is also provided at least one cryogenic matter release actuator configured to release cryogenic matter from said canister.

According to a further teaching of the present invention, said at least one cryogenic matter release actuator is configured as two cryogenic matter release actuators, one said cryogenic matter release actuator being associated with each of said opposing tweezer arms.

According to a further teaching of the present invention, each of said cryogenic matter release actuators is configured to interact with said canister deployed within said opposing tweezer arm with which said cryogenic matter release actuator is associated.

According to a further teaching of the present invention, each of said cryogenic matter release actuators is configured to interact with a displaceable tweezer arm tip deployed within said opposing tweezer arm with which said cryogenic matter release actuator is associated.

According to a further teaching of the present invention, each of said displaceable tweezer arm tips includes one of said cryogenic matter application elements.

There is also provided according to the teachings of the present invention, a method for the application of cryogenic matter directly on a skin lesion while protecting the collateral skin tissue from being damaged by the cryogenic matter, the method comprising: (a) providing an application device having an applicator body configured with opposing tweezer arms, each tweezer arm including a cryogenic matter application element such that when said opposing tweezer arms are closed about the skin lesion, the skin lesion is substantially encased by said cryogenic matter application elements; (b) applying cryogenic matter to each of said cryogenic matter application elements; (c) closing said opposing tweezer arms about the skin lesion, thereby substantially encasing the skin lesion with said cryogenic matter application elements; and (d) removing said application device from the skin lesion.

According to a further teaching of the present invention, said applying cryogenic matter to each of said cryogenic matter application elements is accomplished using a canister of cryogenic matter located outside of said application device.

According to a further teaching of the present invention, said applying cryogenic matter to each of said cryogenic matter application elements is accomplished by using two canisters of cryogenic matter wherein one of said canisters is deployed in each of said tweezer arms.

According to a further teaching of the present invention, said applying cryogenic matter to each of said cryogenic matter application elements is accomplished using two cryogenic matter release actuators, one said cryogenic matter release actuator being associated with each of said opposing tweezer arms.

According to a further teaching of the present invention, each of said cryogenic matter release actuators is implemented so as to interact with said canister deployed within said opposing tweezer arm with which said cryogenic matter release actuator is associated.

According to a further teaching of the present invention, each of said cryogenic matter release actuators is implemented so as to interact with a displaceable tweezer arm tip deployed within said opposing tweezer arm with which said cryogenic matter release actuator is associated.

According to a further teaching of the present invention, said steps (b) and (c) occur substantially simultaneously.

There is also provided according to the teachings of the present invention, a device for the application of cryogenic matter directly on a skin lesion, the device comprising: (a) an applicator body configured with a pair of arms, each arm including a canister containing cryogenic matter; (b) two cryogenic matter release actuators, one said cryogenic matter release actuator being associated with each of said arms; (c) an application tip having at least one cryogenic matter application element extending therefrom; and (d) at least one cryogenic delivery passageway configured in each said arm so as to provide fluid communication between each said canister in each said arm and said cryogenic matter application element; wherein cryogenic matter released from each said canister is delivered to said cryogenic matter application element.

According to a further teaching of the present invention, said application tip is deployed between distal ends of said arms so as to engage both said arms.

According to a further teaching of the present invention, said arms are opposing tweezer arms and said application tip is formed by the tips of said opposing tweezer arms upon closure of opposing tweezer arms.

BRIEF DESCRIPTION OF THE DRAWINGS

The invention is herein described, by way of example only, with reference to the accompanying drawings, wherein:

FIG. 1 is a front view of the invention of a first preferred embodiment of an applicator system constructed and operational according to the teachings of the present invention;

FIG. 2 is a cross sectional view of the applicator system of FIG. 1;

FIG. 3 is a perspective view of the tweezers applicator of the applicator system of FIG. 1;

FIG. 4 is a top perspective view of a canister cap of the applicator system of FIG. 1;

FIG. 5 is a top perspective view of a nozzle unit of the applicator system of FIG. 1;

FIG. 6 is a front perspective view of the tweezers inserted in the nozzle unit of the applicator system of FIG. 1;

FIG. 7 is an enlarged detail of area B of FIG. 2;

DESCRIPTION OF THE PREFERRED EMBODIMENTS

Figure 8:
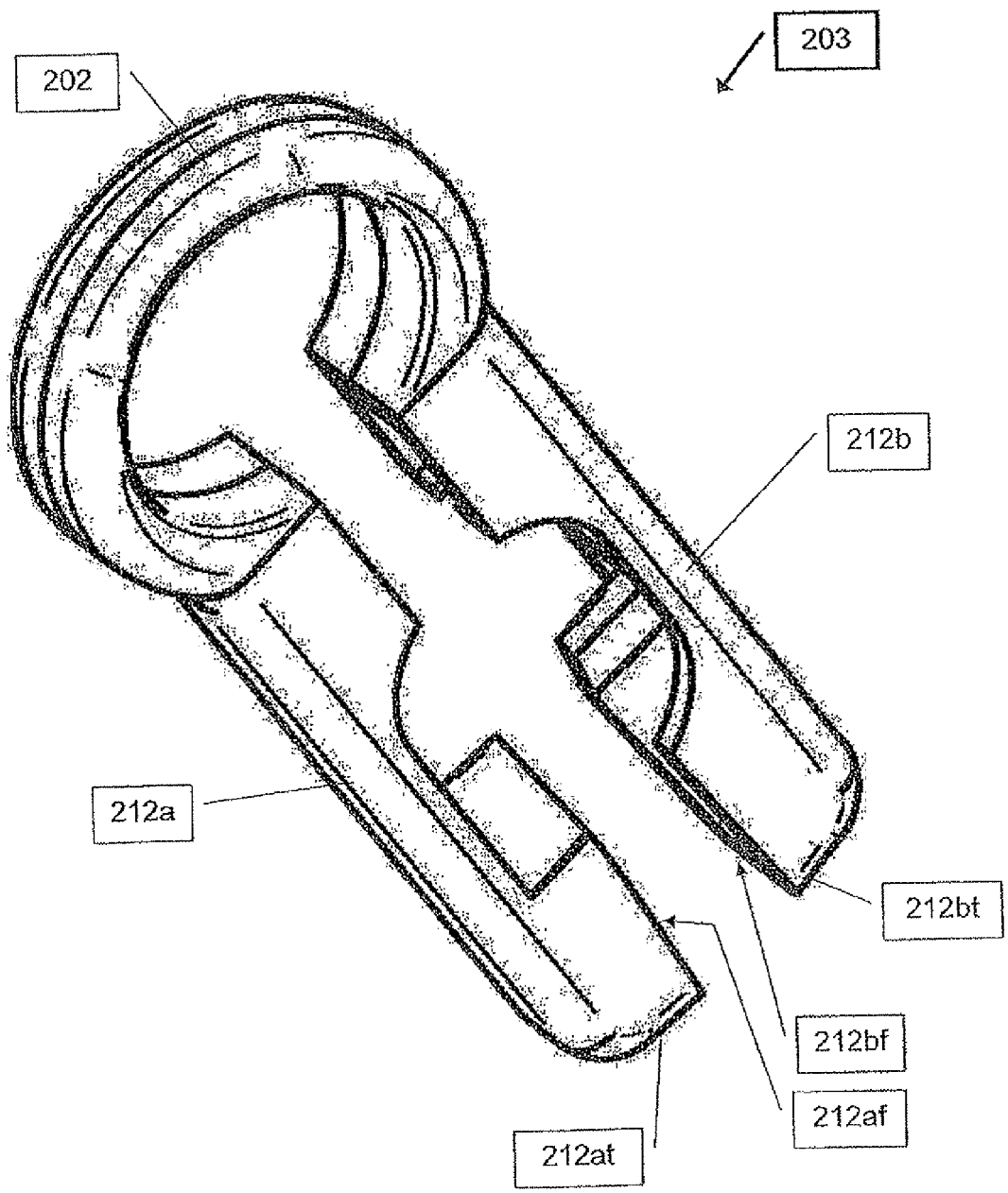
FIG. 8 is an enlarged detail of the tweezers applicator of the applicator system of FIG. 1.

The present invention is a tweezers type device and method for the application of cryogenic matter directly on a skin lesion while protecting the collateral skin tissue from being damaged by the cryogenic matter.

The principles and operation of a tweezers type device and method for the application of cryogenic matter directly on a skin lesion according to the present invention may be better understood with reference to the drawings and the accompanying description.

By way of introduction, in its simplest form, the cryogenic applicator of the present invention is a tweezer type applicator configured such that when the tweezer arms are closed upon each other, the skin lesion, commonly referred to as a "skin tag," is substantially encapsulated and isolated from the surrounding skin tissue. Therefore, when the cryogenic matter is applied to the lesion, the surrounding collateral skin tissue is protected from contact with the cryogenic matter.

Referring now to the drawings, FIGS. 1-8 illustrate the basic tweezer type applicator of the present invention. In this first preferred embodiment of the present invention, the tweezer arms 212a and 212b are attached one to another by the spring element 202. The tweezer arms 212a and 212b are configured such that when closed upon each other, at least the portion of the interior faces 212af and 212bf in the area close to the tip of each tweezer arm 212a and 212b respectively are substantially parallel such that the interior faces 212af and 212bf are able to close substantially tightly. With such a configuration, when the tweezer arms are closed, the target skin lesion is substantially isolated and the tips 212at and 212bt of the tweezer arms protect the collateral skin tissue during the cryogenic treatment.

The cryogenic refrigerant 214 is stored in a pressurized canister 206. A nozzle unit 208 is attached over the end of the canister on top of the release valve. A canister cap 205 is inserted over a beaded edge of the canister. The canister cap 205 contains two tweezer opening guides 210 through which tweezers 203 may be inserted.

The tweezers 203, comprised of two substantially parallel tweezers arms 212a and 212b, are connected by a spring 202. Absorbent buds 201 with handles 217 are inserted within the tweezers proximate to each tweezer arm tips 212at and 212bt.

The refrigerant flows through the release valve and then through a nozzle outlet 208 laterally. Refrigerant is absorbed by the absorbent buds 201 inserted within the tweezers 203. Excess cryogenic gas or liquid that accumulates will be drained through the refrigerant drain 211. The tweezers containing the absorbent buds with refrigerant can then be applied to the skin lesion to freeze it resulting in its destruction.

An embodiment of the tool for treatment of skin lesions utilizing cryogenic agents is shown in FIGS. 1-8. The method for treatment of skin lesions removes skin lesions by substantially reducing the temperature of the lesion tissue on the subject's body, resulting in the destruction of the lesion tissue within a few days. A tweezers 203 included on the method for treatment of skin lesions acts as a buffer between the patient's healthy skin and the cryogenic agents contained in the invention.

The refrigerant 214 is comprised of a cryogenic agent such as dimethyl ether (DME) and propane, or other cryogenic material. It is stored in a pressurized canister 206. In one embodiment of the invention, the pressurized canister 206 may be comprised of a cylindrically shaped metallic container. A canister cap 205 is attached over the end of the canister 206 and serves to hold the tweezers 203 in place, and also prevents the spraying of cryogenic matter. A nozzle unit 207 is attached at one end of the canister 206 proximate to the release valve 218. The canister cap 205 contains two tweezer opening guides 210 comprised of apertures through which the tweezer 203 may be inserted.

The tweezers 203 are comprised of two substantially parallel tweezer arms 212a and 212b connected by a spring 202 which holds the tweezer arms 212a and 212b in an open position. An absorbent bud 201, including a handle 217 affixed to the absorbent bud, is attached proximate to each tweezer tip 212at and 212bt. An access point 221 on the tweezers allows the user to insert and remove the absorbent buds 201 using the handle 217. Each tweezer arm 212a and 212b contains an absorbent bud insertion guide 204 which facilitates insertion of the absorbent bud 201 into the tweezer 203. A baffle 213 in the tweezers prevents refrigerant 214 from flowing out of the canister cap 205. The tweezers also contains a rib 215 to support the absorbent bud handle 217. The tweezer tips 212at and 212bt depress the nozzle unit 207 and also act as a barrier between the skin and the refrigerant 214.

The refrigerant 214 initially flows through the release valve 218 and then through the nozzle outlets 208. After leaving the nozzle outlets 208, refrigerant 214 flows through a plurality of nozzle outlets 208, thereby causing refrigerant 214 to flow directly onto the absorbent buds 201. A plurality of refrigerant drains 211 in the nozzle unit 207 drain excess refrigerant 214.

To remove a skin lesion using the method for treatment of skin lesions of the present invention, a user inserts the tweezers 203 with their buds 201 into the tweezer opening guides 210 thereby stabilizing the tweezers 203 in the tweezer guides 216. The user then presses down on the tweezers 203, thereby depressing the nozzle unit 207. The pressurized refrigerant 214 then flows through the release valve 218 and through the nozzle outlets 208. The absorbent buds 201 are thereby saturated with refrigerant 214. The refrigerant drains 211 release excess refrigerant 214. The user removes the tweezers 203 from the canister cap 205, and then squeezes the skin lesion, thus completely encapsulating the skin lesion between the tweezer buds 201 containing refrigerant 214. The temperature of the lesion tissue is substantially reduced as a result of applying the tweezer buds 201, causing tissue destruction so that the lesion tissue will normally fall off within several days. In some embodiments of the invention, the absorbent buds 201 are normally replaced after each use of the method for treatment of skin lesions of the present invention.

As will be understood from the following description of variant embodiments of the present invention, this basic tweezer configuration as illustrated in FIGS. 1-8 may be adapted for use with any number of cryogenic application embodiments.

Figure 9:
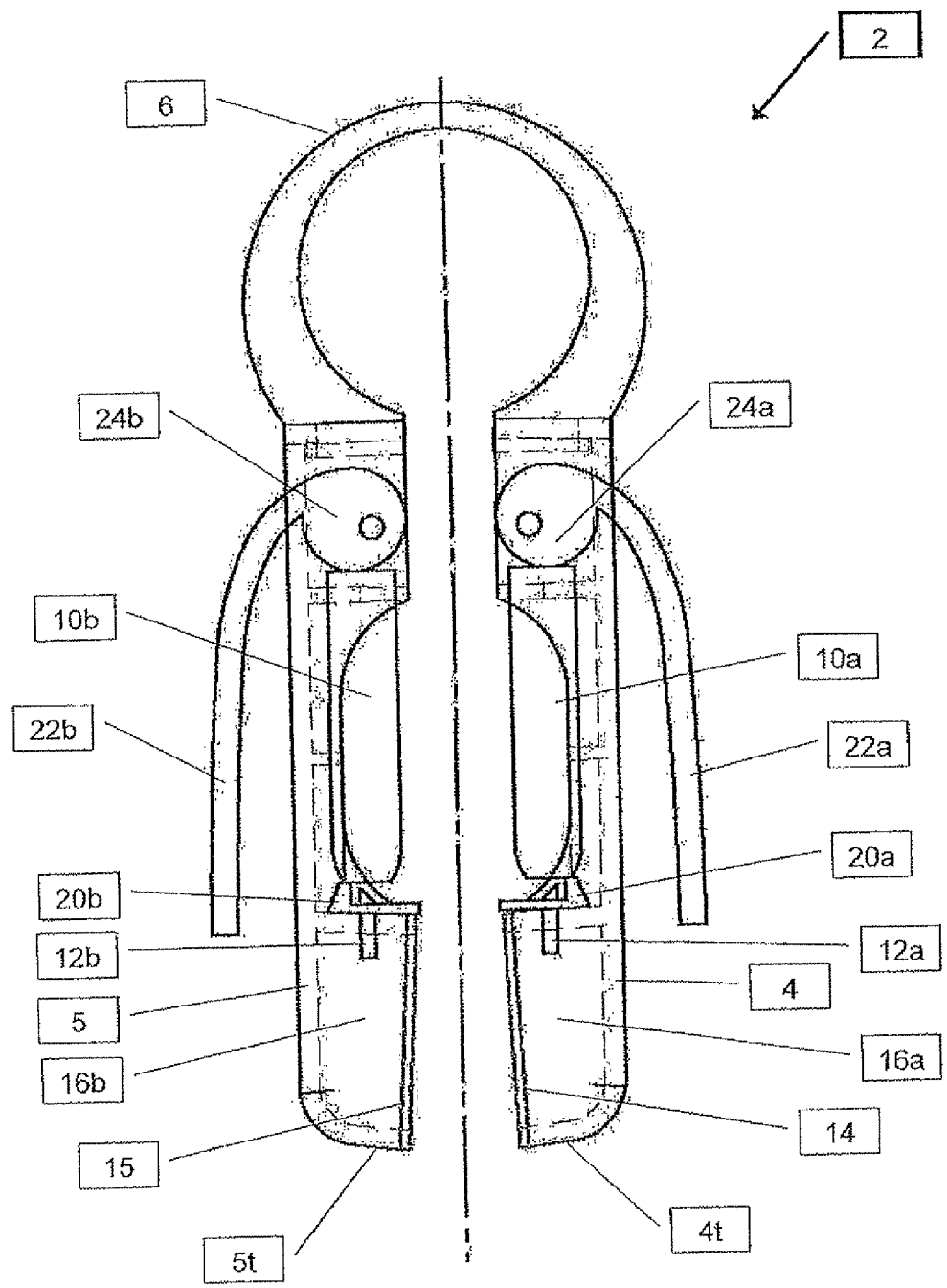
FIG. 9 is a cross-sectional side elevation of a second preferred embodiment of the applicator of the present invention.

The second preferred embodiment 2 of the present invention illustrated in FIG. 9 is configured such that the cryogenic matter is stored in two pressurized canisters 10a and 10b that are deployed in tweezer arms 4 and 5 respectively. It is intended that the pressurized canisters 10a and 10b will be punctured by hollow needles 12a and 12b. Canister retaining elements 20a and 20b are deployed in each of the tweezer arms in order to prevent premature penetration of the canisters by the needles. As illustrated here, at least a portion of each of the canister retaining elements 20a and 20b extends beyond the interior faces 14 and 15 of tweezer arms 4 and 5.

In operation, when the tweezer arms are close around a target lesion, the canister retaining elements 20a and 20b are displaced allowing the canisters 10a and 10b to be forced against the points of the hollow needles 12a and 12b. This is accomplished by pressing levers 22a and 22b toward the tweezer arms, thereby rotating cams 24a and 24b. The cryogenic matter stored in each of the canisters is directed through the hollow needles into chambers 16a and 16b located in the tips of each of the tweezer arms.

In this embodiment of the present invention, at least a portion of the interior faces 14 and 15 of tweezer arms 4 and 5 are configured with a permeable material such as, but not limited to, foam that allows the cryogenic matter released into chambers 16a and 16b to reach the target lesion.

Figure 10:
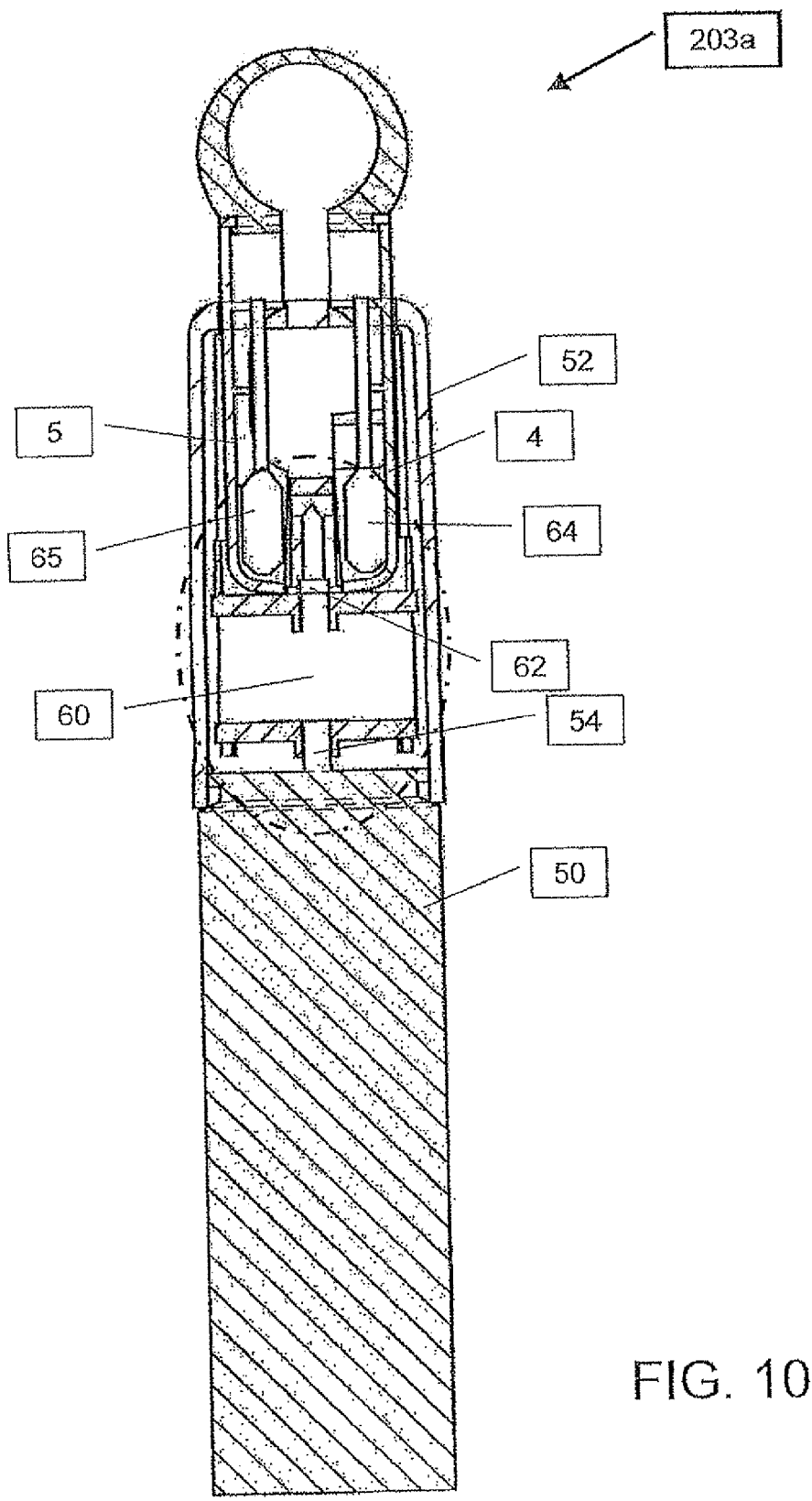
FIG. 10 is a cross-sectional side elevation of a third preferred embodiment of the applicator of the present invention, shown here as part of a system.
Figure 11:
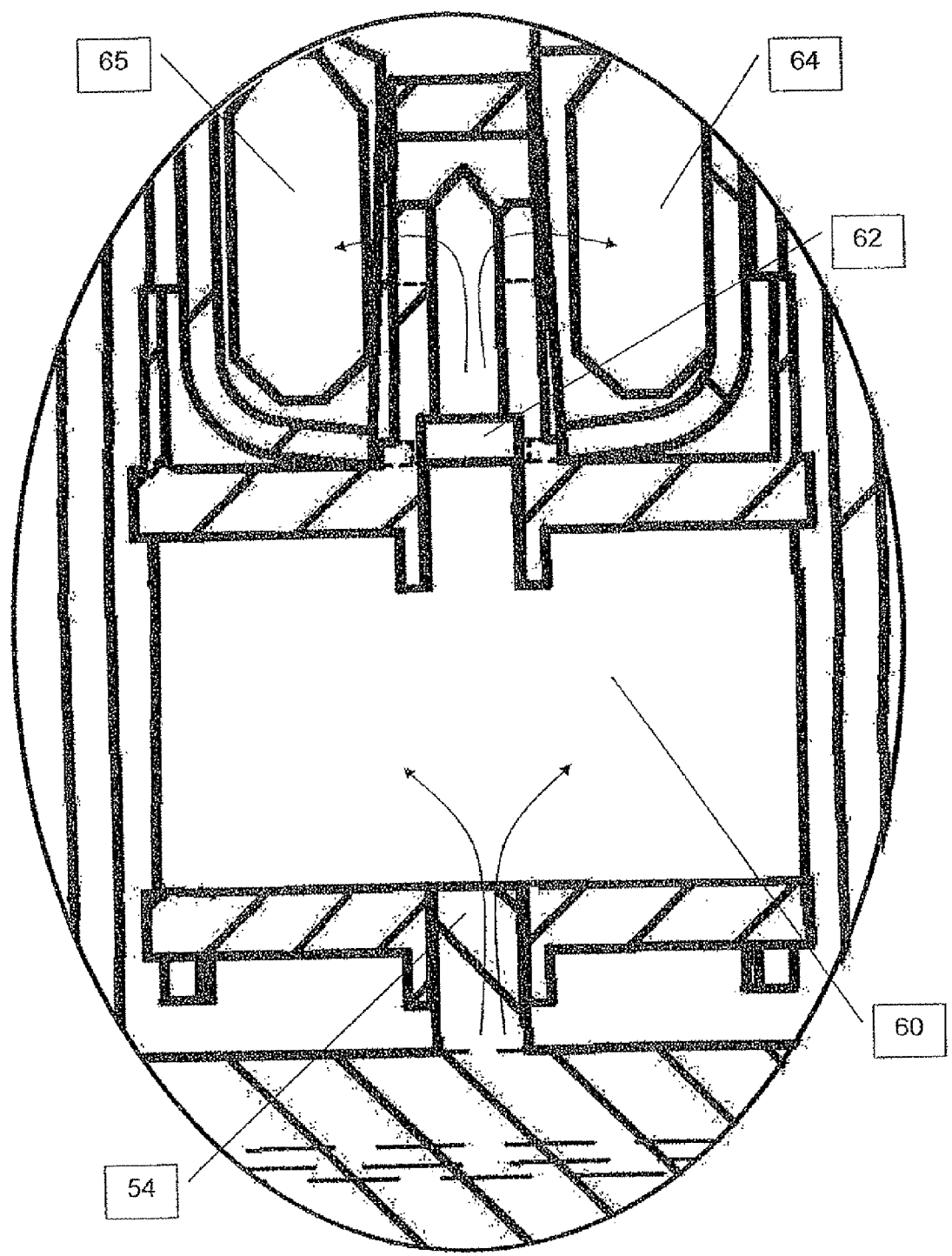
FIG. 11 is a detail of the embodiment of FIG. 10.

The third preferred embodiment of the present invention illustrated herein in FIGS. 10 and 11, is closely related to the embodiment described with regard to FIGS. 1-8 in that the tweezer arms 4 and 5 of the tweezer applicator 203a are configured with absorbent applicator buds 64 and 65. In order to apply Cryogenic matter to the applicator buds, the tweezer arms are inserted in the canister cap 52 that is deployed on pressurized canister 50 that contains the cryogenic matter. Once the tweezer arms are inserted into the canister cap, one-way valve 54 is operated thereby allowing cryogenic matter to enter the dosing chamber 60 which is designed to hold a predetermined dose of the cryogenic matter. When the dosing chamber is filled, one-way valve 62 is operated so as to direct the cryogenic matter onto the applicator buds, thereby saturating them with the cryogenic matter.

The applicator 203a is then removed from the canister cap 52 and the tweezer arms are closed around the target skin lesion.

Figure 12:
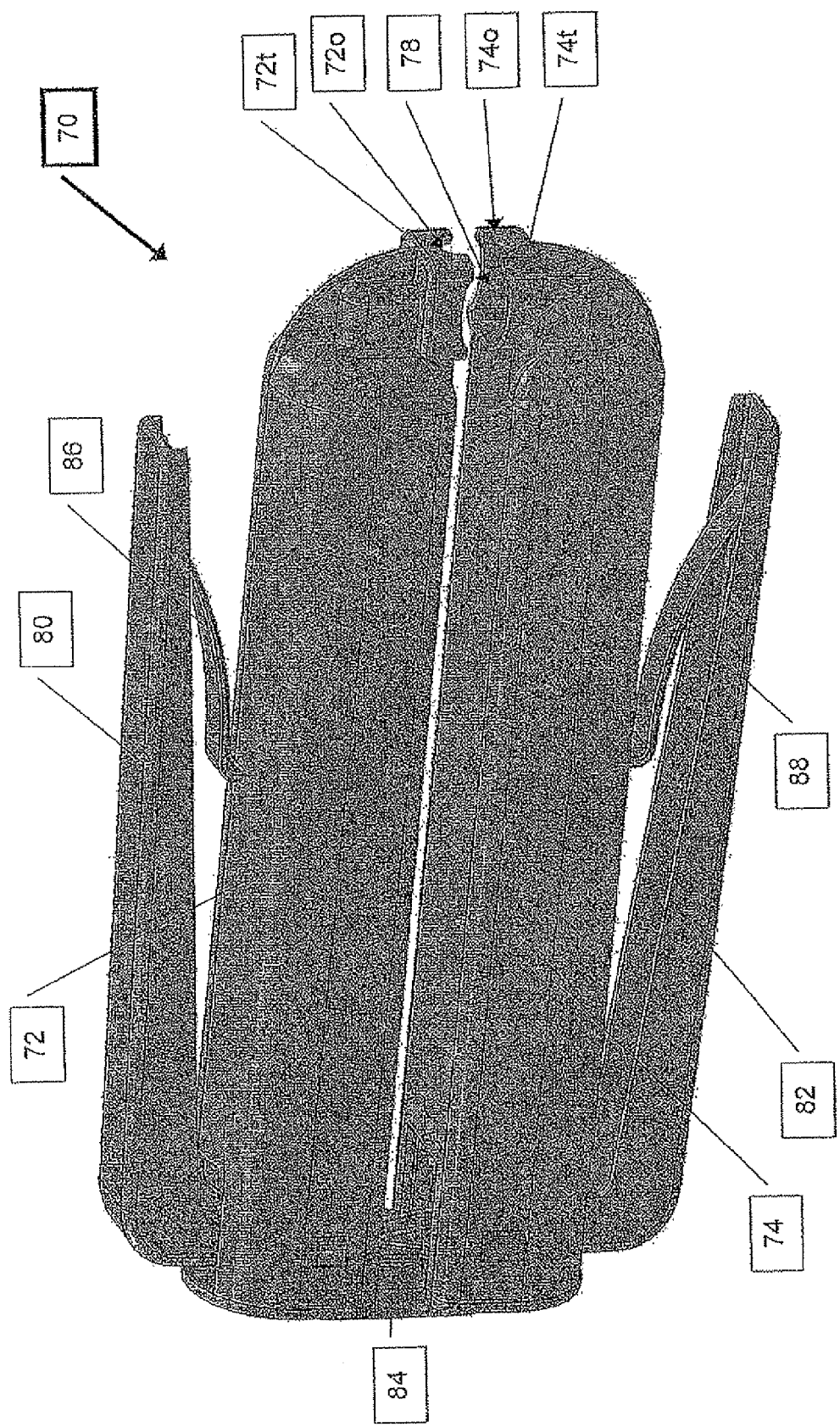
FIG. 12 is an isometric side view of a fourth preferred embodiment of a tweezer type cryogenic applicator constructed and operational according to the teachings of the present invention.
Figure 13:
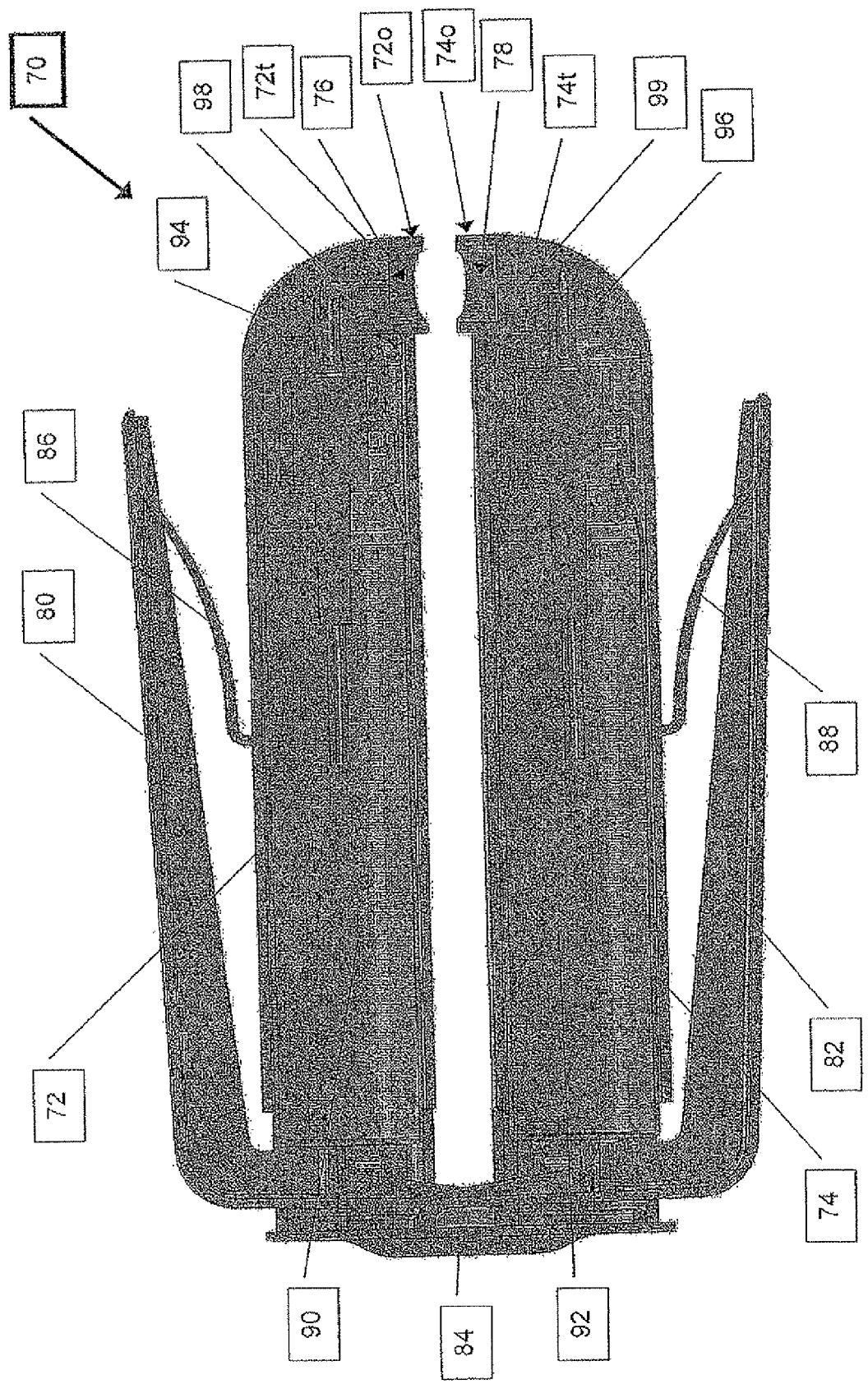
FIG. 13 is a cross sectional view of the applicator of FIG. 12.
Figure 14:
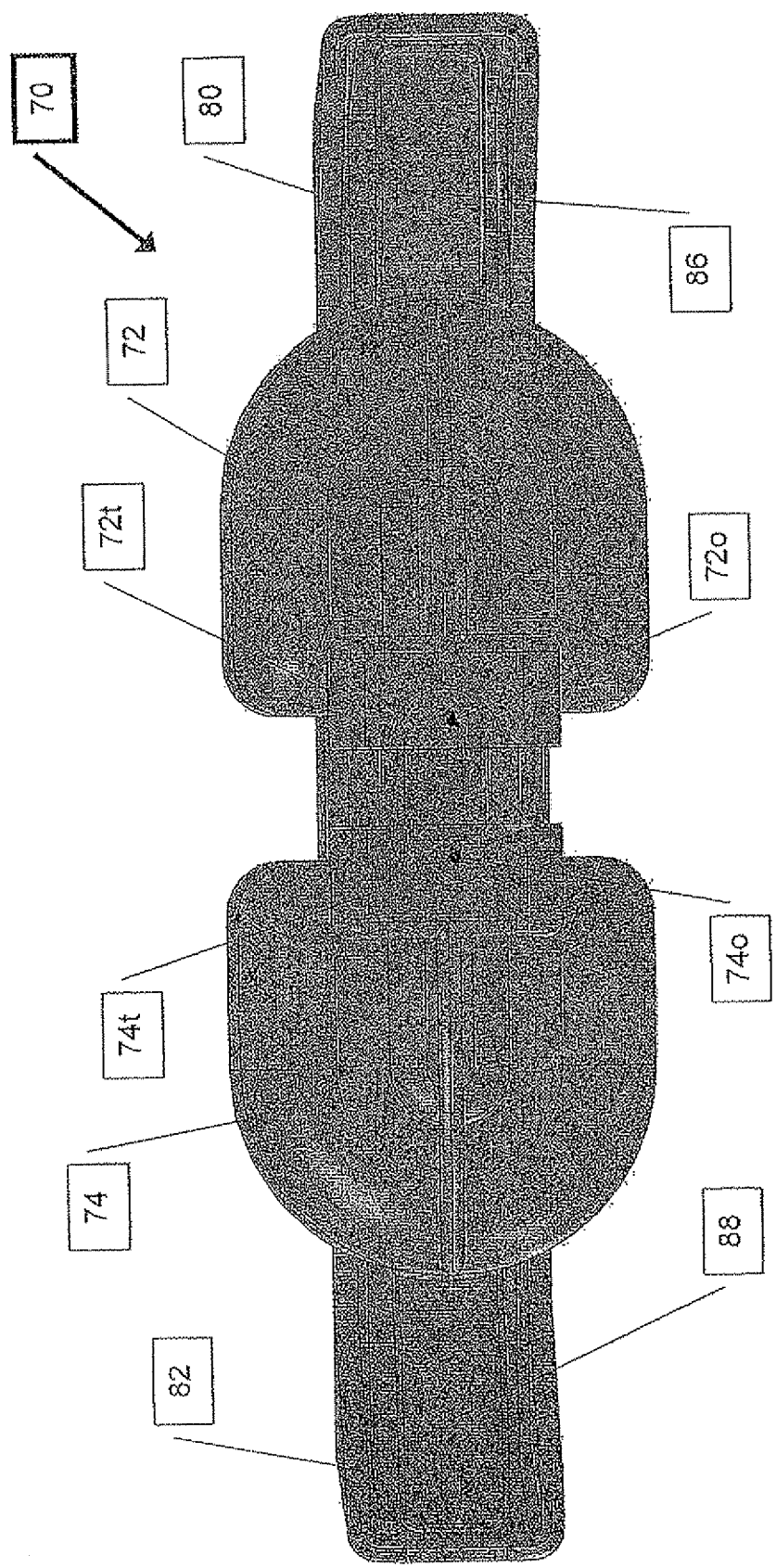
FIG. 14 is an end elevation of the embodiment of FIG. 12.

The fourth preferred embodiment 70, as shown in FIGS. 12-14, illustrates a design using levers 80 and 82 built into the end cap 84, which also serves to connect the two tweezer arms 72 and 74. In order to ensure the tweezers are closed before the valves of the canisters, which are deployed in each of the two tweezer arms 72 and 74 and contain the cryogenic material, open, leaf spring like elements 86 and 88 extend from the tweezer arms 72 and 74. Leaf spring elements 86 and 88 may be integrally form with each side piece at the time of production or attached during assembly. As the levers 80 and 82 are squeezed, the leaf spring elements 86 and 88 are engaged so as to close the tweezer arms 72 and 74 such that the tips 72t and 74t close around the lesion. As more pressure is applied to the levers 80 and 82, the canisters 90 and 92 of cryogenic matter is forced forward as each of the levers 80 and 82 pivots about its hinged connection to the base 84. This action causes the valves 94 and 96 of each of the canisters 90 and 92 to open, thereby releasing at least a portion of the cryogenic material. Preferably, but not necessarily, the canisters 90 and 92 are configured with valves 94 and 96 that deliver a metered dose, thereby assuring that only a predetermined amount of cryogenic matter is released while also allowing for multiple use of the applicator. It should be noted that the use of a metered dose is intended only as a non-limiting example and that a non-metered continuous delivery of cryogenic matter is within the scope of the present invention.

The cryogenic matter that is released moves through passages 98 and 99 and enters regions 76 and 78 that open one to another such that the absorbent material deployed in each region 76 and 78 contact each other when the tweezer arms 72 and 74 are in a closed deployment. While it is preferable, it is not necessarily that at least one of regions 76 and 78 has deployed within it absorbent material that is substantially saturated with the cryogenic matter.

Figure 15:
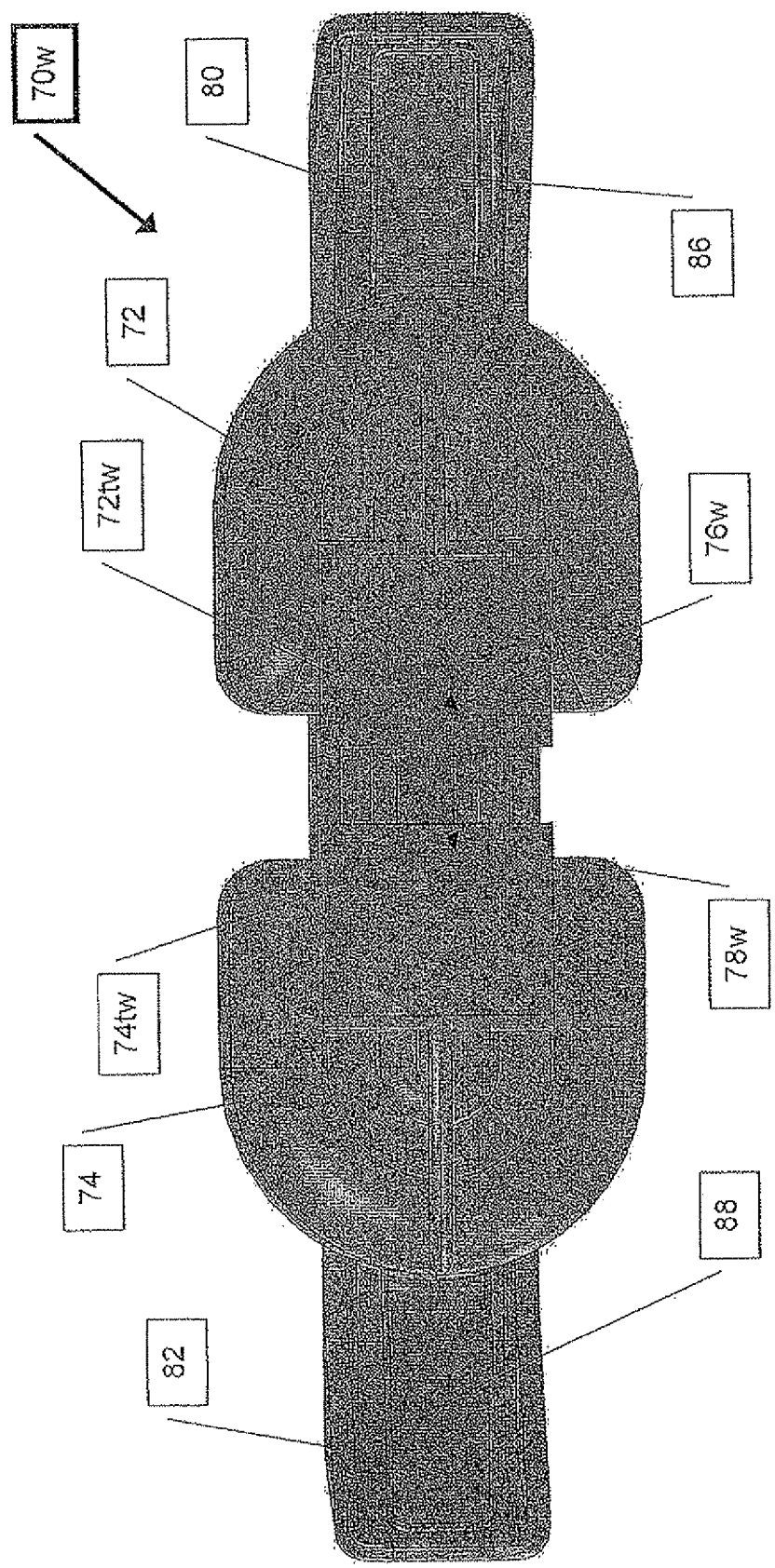
FIG. 15 is an end elevation of the embodiment of FIG. 12 modified for use on warts.
Figure 16:
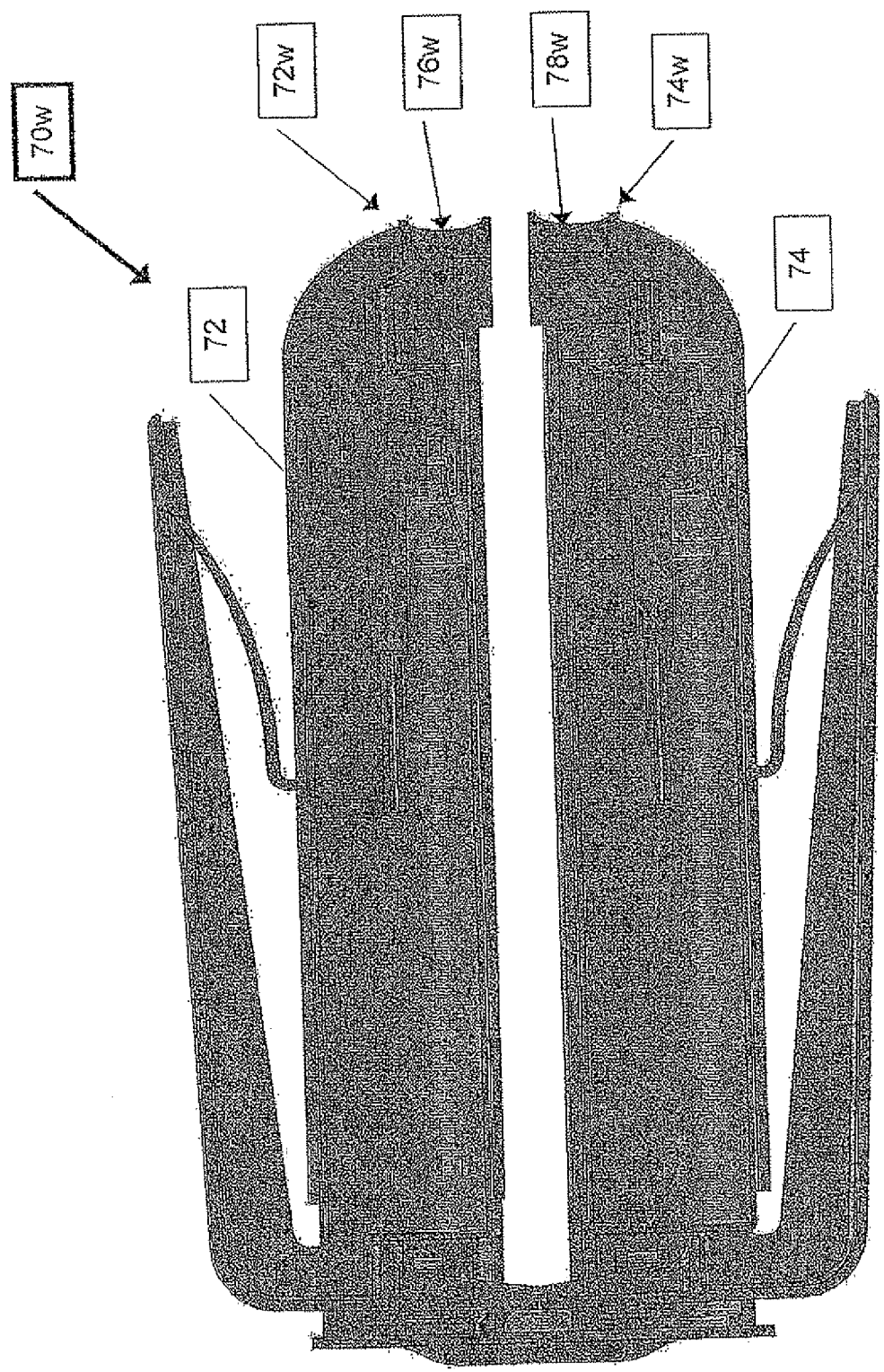
FIG. 16 is a cross sectional view of the embodiment of FIG. 15.

When treating lesions such as, but not limited to, skin tags, the lesion is encapsulated by the absorbent material when the cryogenic matter saturates the absorbent material. However, if the treatment target is a wart, the variant embodiment 70w of the tweezers of the present invention as illustrated in FIGS. 15 and 16 should be used.

As illustrated here, the regions 76w and 78w are open both to each other and on their outer sides as well, such that the absorbent material deployed in each of the region 76w and 78w is exposed at the tips 72tw and 74tw.

With such a configuration, when the tweezer arms 72 and 74 are closed and the absorbent material is saturated, the tweezer tips 72tw and 74tw, which now form an application tip, are kept closed and contact between the absorbent material and the wart is made.

Figure 17:
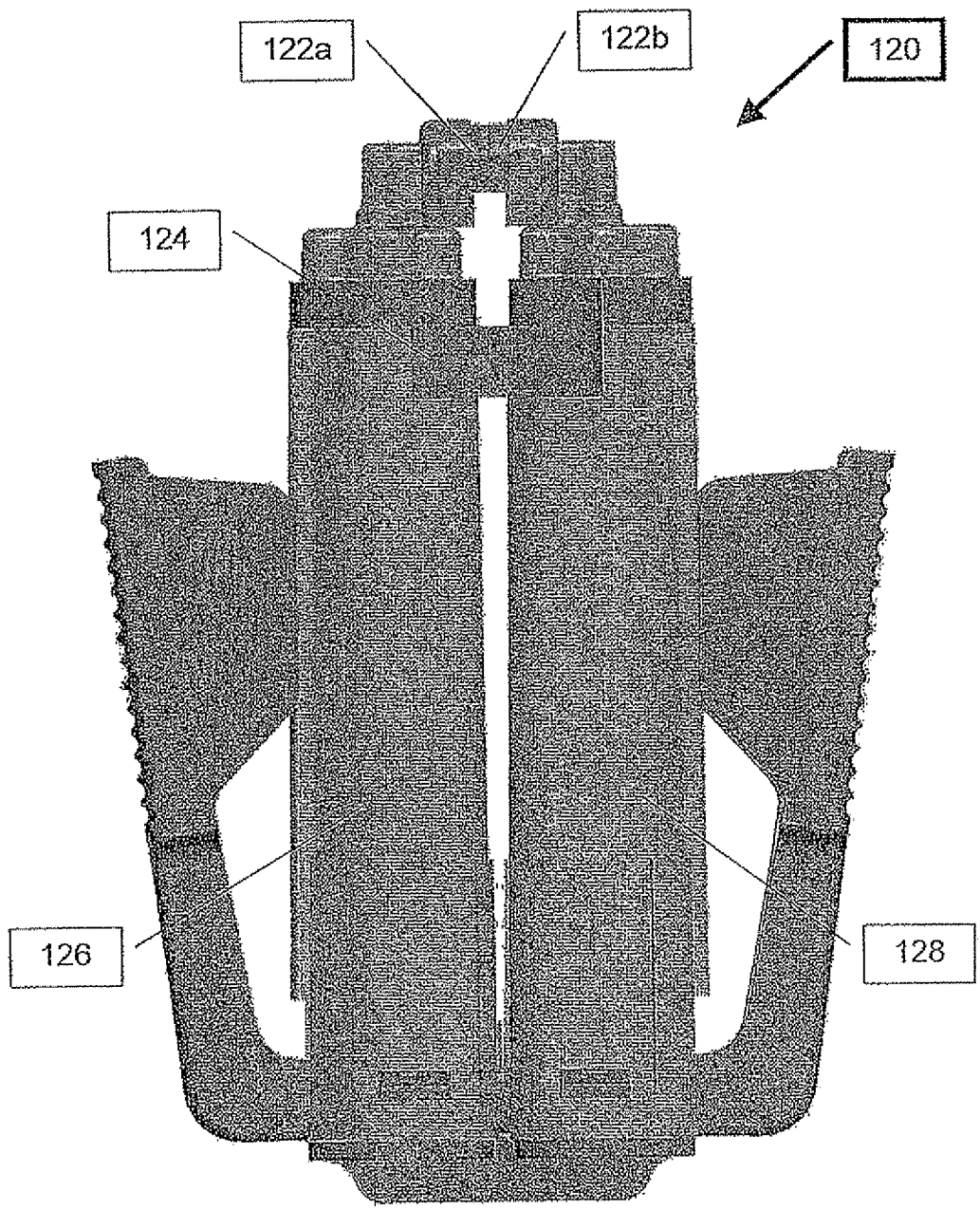
FIG. 17 is a side elevation of a variant embodiment of the embodiment of FIG. 12.

FIG. 17 illustrates a variant 120 of the embodiment of tweezer applicator of FIGS. 12-14. FIG. 17 shows the cryogenic matter application elements 122a and 122b. As illustrated is the additional alignment element 124 which provides alignment for the tweezer arms 126 and 128.

Figure 18:
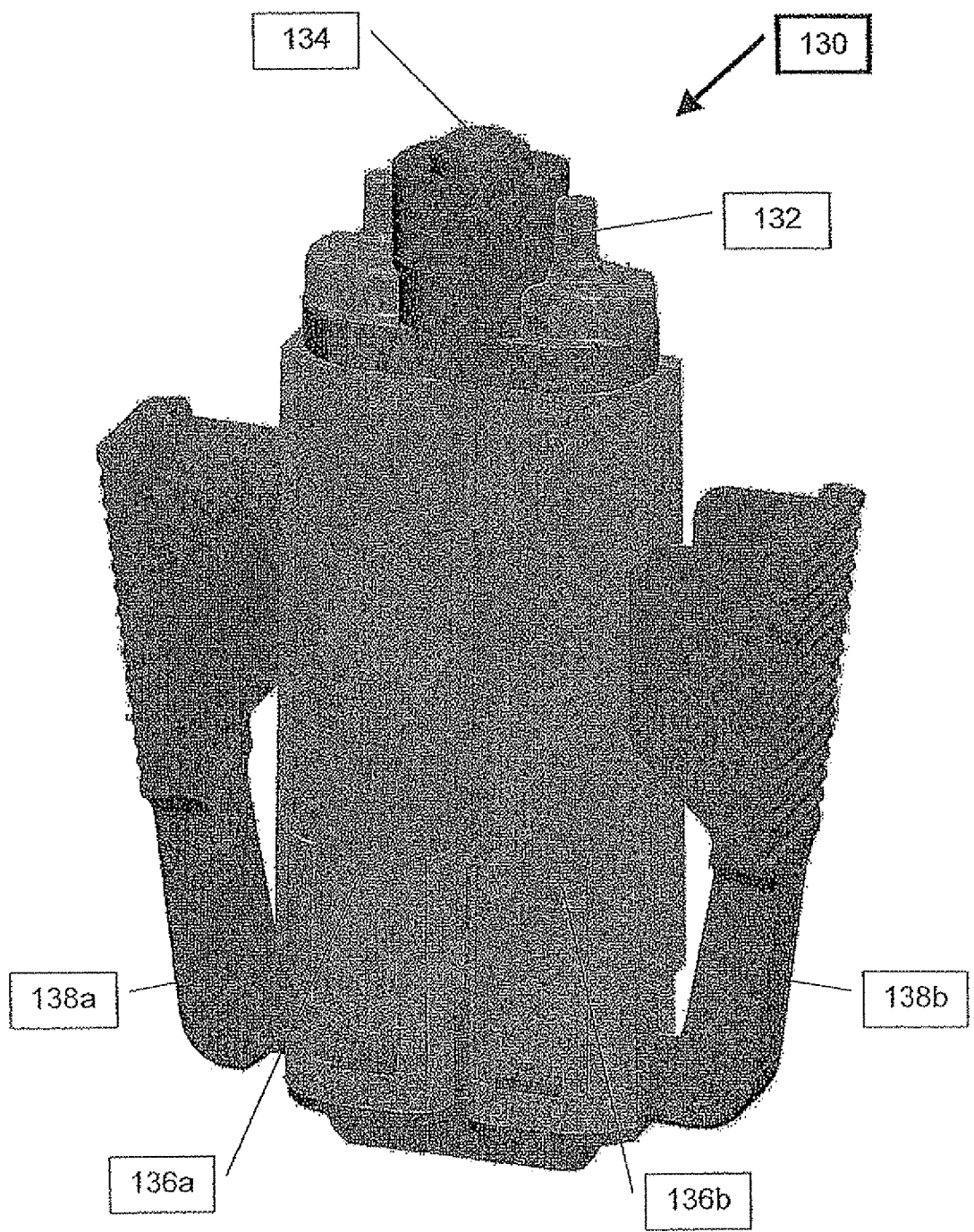
FIG. 18 is a perspective view of a variant embodiment of the embodiment of FIG. 15.

FIG. 18 illustrates a variant 130 of the embodiment of tweezer applicator of FIGS. 15-16. FIG. 18 shows a device for the application of cryogenic matter directly on a skin lesion having a single cryogenic matter application element 134 extending from the end of the wart applicator tip 132 deployed between distal ends of the arms so as to engage both of the arms. More specifically, the applicator of FIG. 18 has an applicator body configured with a pair of arms 136a and 136b, each arm including a canister containing cryogenic matter (not shown). There are two cryogenic matter release actuators 138a and 138b, one the cryogenic matter release actuator being associated with each of the arms. There is at least one cryogenic delivery passageway configured in each the arm so as to provide fluid communication between each the canister in each the arm and the cryogenic matter application element such that cryogenic matter released from each of the canister is delivered to the cryogenic matter application element.

By way of a practical means for producing this embodiment of the present invention, the wart applicator tip 132 is constructed so as to be deployable on the distal ends of the tweezer arms of the embodiment of FIG. 17.

It will be understood that the embodiments described above with regard to FIGS. 9-18 include cryogenic matter release actuators configured to interact with the canister deployed within the opposing tweezer arm with which the cryogenic matter release actuator is associated.

FIGS. 19-22 illustrate a further variant 140 of the tweezer applicator of the present invention in which the cryogenic matter release actuators are configured to interact with the displaceable tweezer arm tip deployed within said opposing tweezer arm with which said cryogenic matter release actuator is associated.

Figure 19:
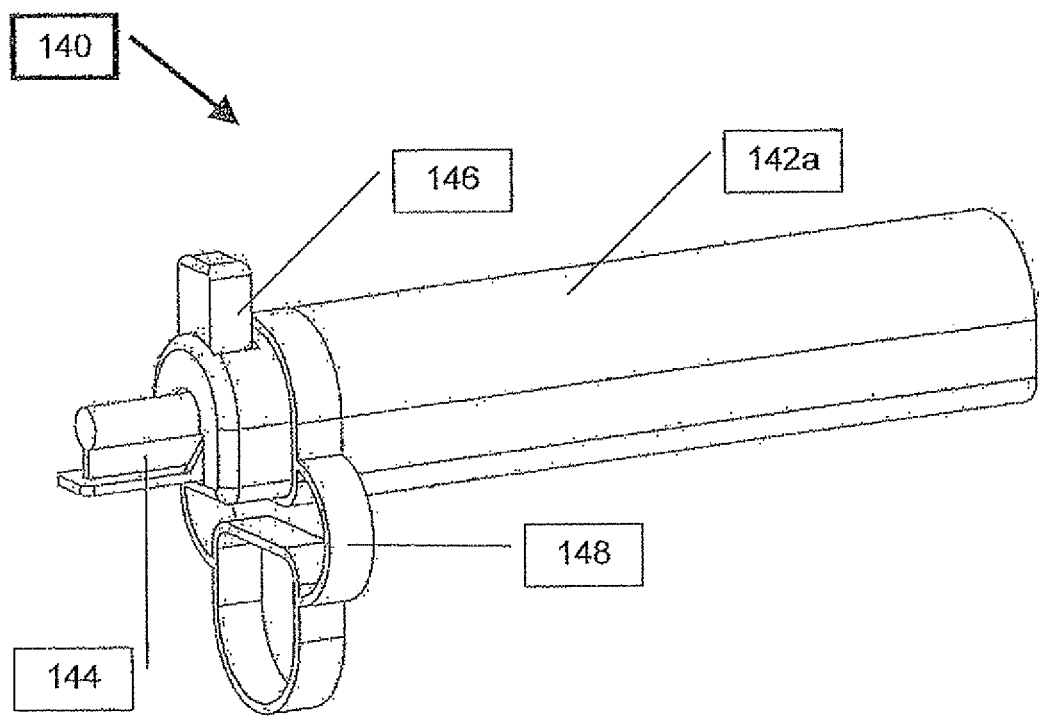
FIGS. 19 and 20 are perspective views of a portion of a further variant embodiment of the embodiment of FIG. 12.
Figure 20:
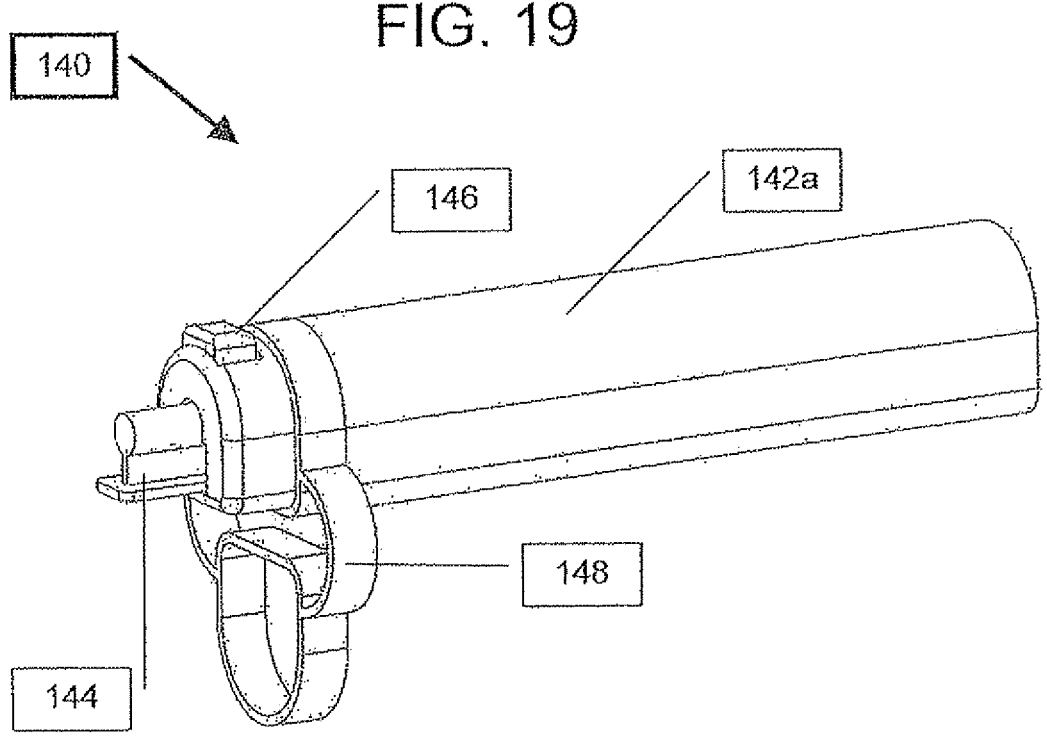
Figure 21:
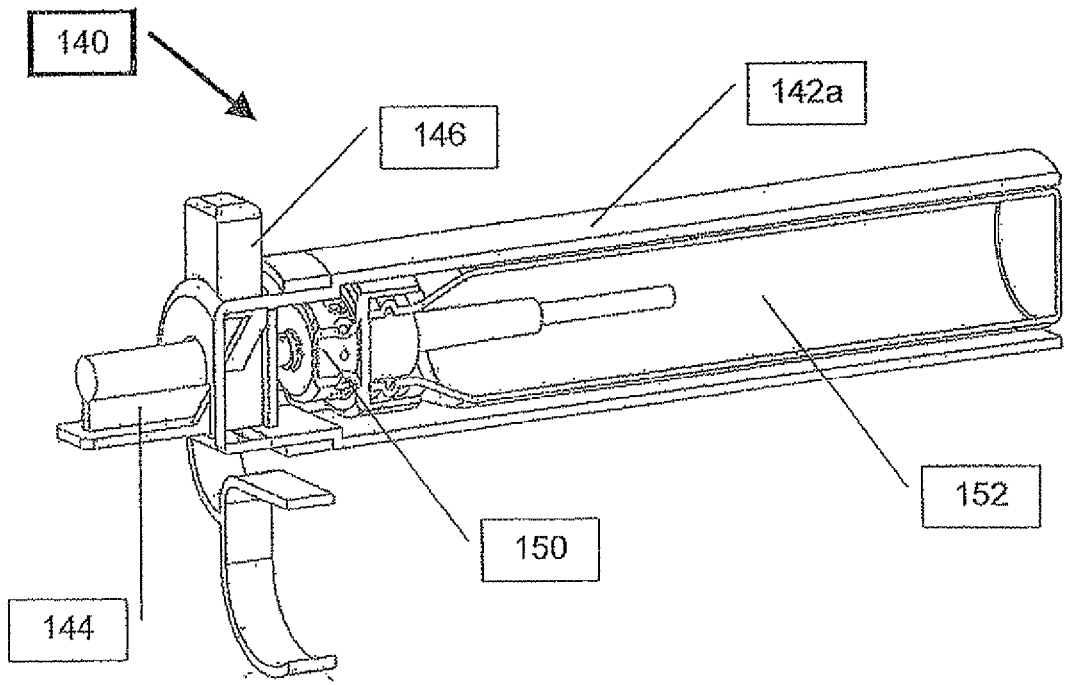
FIG. 21 is a perspective section view of the embodiment of FIG. 19.
Figure 22:
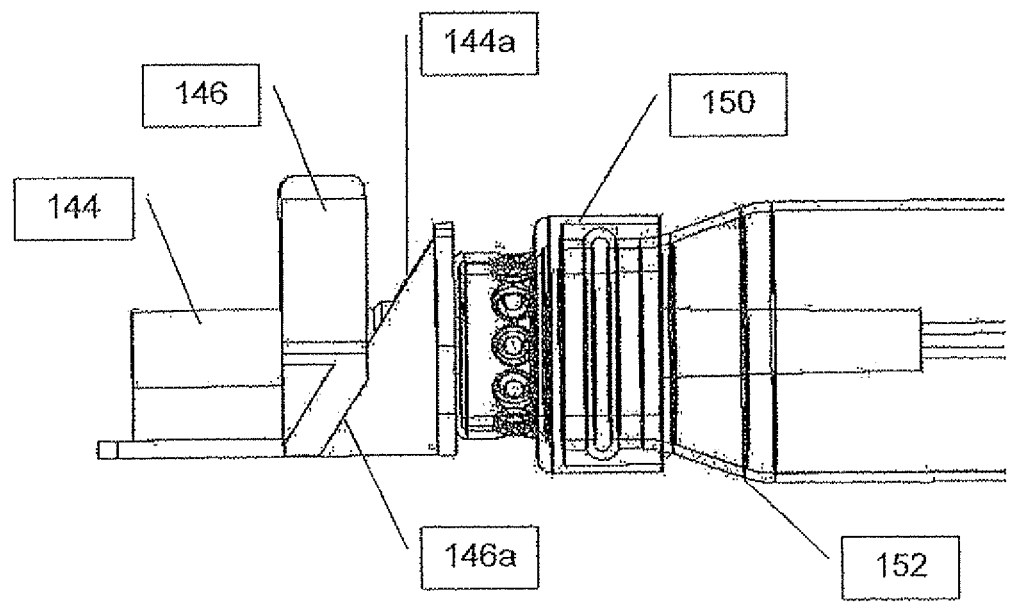
FIG. 22 is a side section detail of FIG. 21.

Illustrated here is only one 142a of the two opposing tweezer arms supported by spring element 148. In this embodiment, inward displacement of the trigger button 146 causes the inward displacement of the displaceable tweezer arm tip 144, as seen in the comparison of FIGS. 19 and 20. The inward displacement of displaceable tweezer arm tip 144 activates the dispenser nozzle 150 deployed on the canister 152 of cryogenic matter.

While there are numerous configurations of the association of the trigger button 146 and the displaceable tweezer arm tip 144, the embodiment illustrated here is configured such that the interaction between the sloped surface 146a of trigger button 146 and the corresponding sloped surface 144a of displaceable tweezer arm tip 144 causes inward displacement of the displaceable tweezer arm tip 144 when the trigger button 146 is pressed inwardly. Once the cryogenic matter application elements (not shown) associated with the tweezer arms have been saturated with sufficient cryogenic matter, the trigger buttons are released thereby allowing the displaceable tweezer arm tips to return to their original deployment in preparation for application on the skin lesion.

Figure 23:
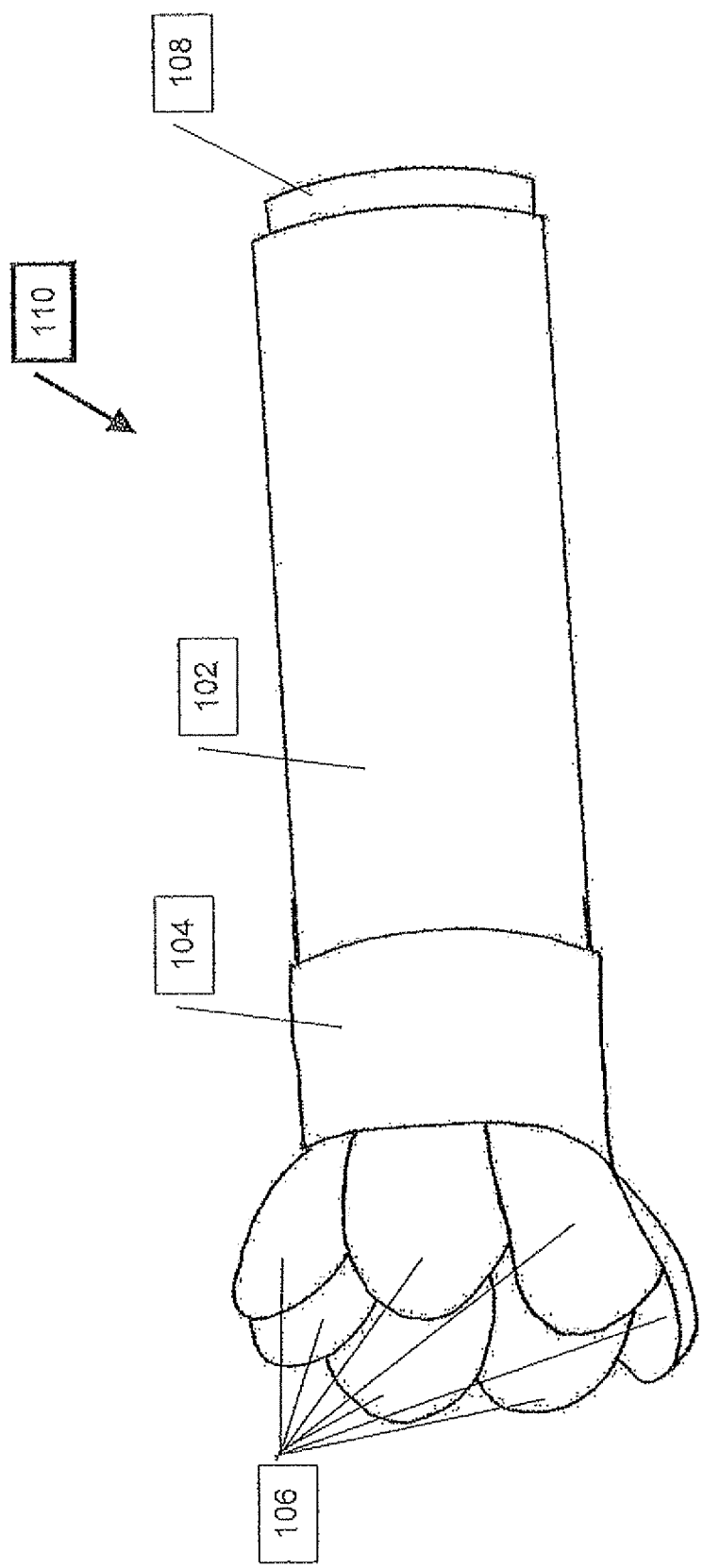
FIG. 23 is an isometric view of a fifth embodiment of an applicator constructed and operational according to the teachings of the present invention, this embodiment having an adjustable opening tip shown here in an open deployment.
Figure 24:
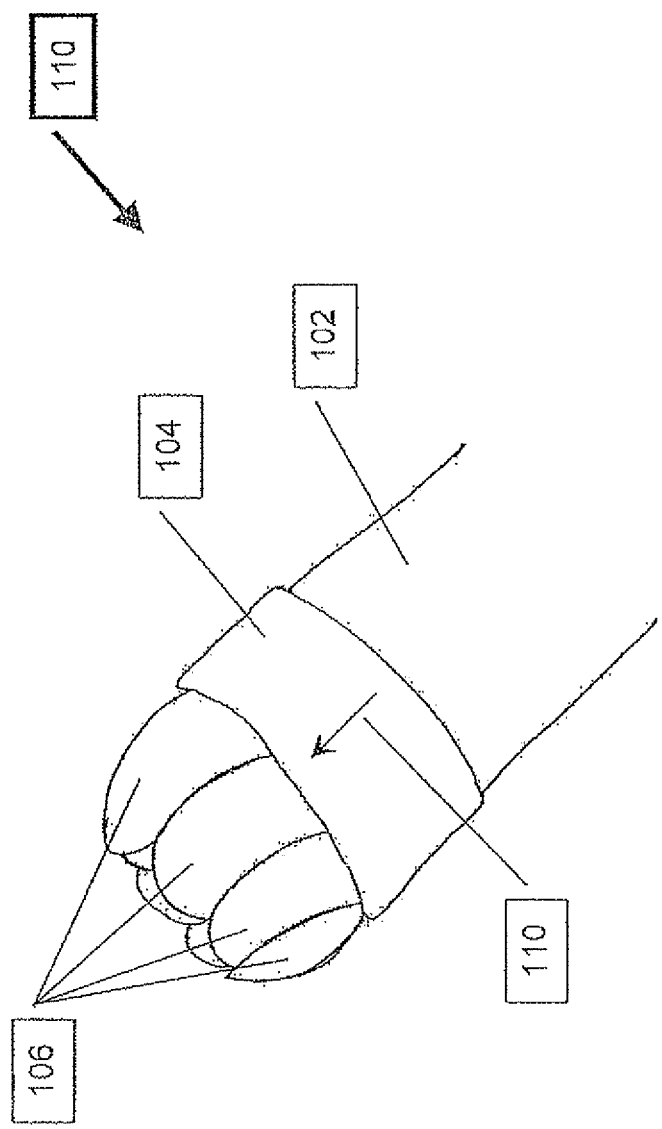
FIG. 24 is an isometric view of the embodiment of FIG. 23 shown in a closed deployment.

The fifth embodiment 110 of an applicator of the present invention is illustrated in FIGS. 23-24. This pen-style embodiment, which is preferably for use with skin tags, has a substantially hollow applicator barrel 102 to which is connected an array of adjustable fingerlike extensions 106 shown in FIG. 23 in an open deployment and in FIG. 24 in a closed deployment. Adjustment of the fingers 106 is accomplished by sliding adjustment collar 104 lengthwise along the barrel 102.

Similar to the embodiments described above, here too, a canister of cryogenic matter is deployed in the barrel 102. The canister valve is activated by simply pushing the activation button 108.

In operation, the applicator 110, with the fingers 106 in an open deployment, is positioned such that the fingers substantially surround the target skin tag. Adjustment collar 104 is then slid toward the fingers 106 as illustrated by arrow 110 in FIG. 24, thereby closing the fingers 106 around the skin tag so as to protect the surrounding skin tissue from collateral damage when the cryogenic matter is applied to the skin tag.

This embodiment may include absorbent material deployed in the barrel 102 near the fingers 106 so as to come into contact with the skin tag. Alternatively, the cryogenic matter may be applied directly to the skin tag since the fingers 106 protect the surrounding skin tissue from collateral damage.

Figure 25:
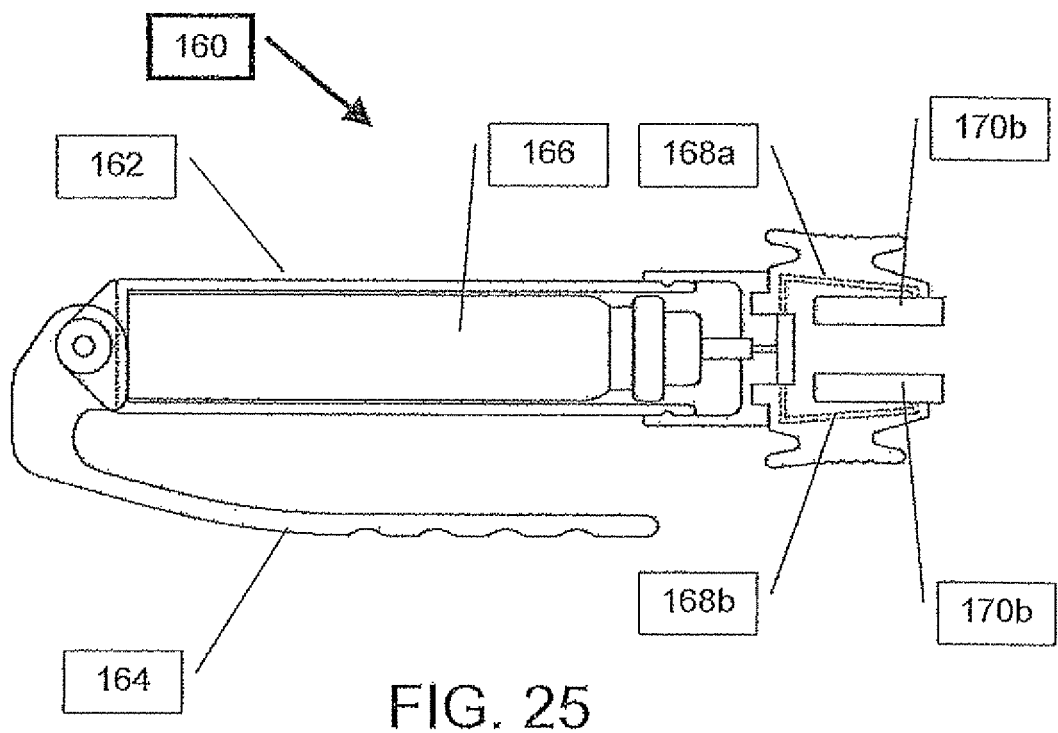
FIG. 25 is a side sectional view of a sixth embodiment of an applicator constructed and operational according to the teachings of the present invention

FIG. 25 illustrates a sixth preferred embodiment 160 of the present invention for use with skin tags is a second pen-style applicator. This embodiment includes a single cylindrical body 162 to which is attached a single actuator handle 164. Cryogenic matter leaving the canister 166 travels through passageways 168a and 168b to the cryogenic matter application elements 170a and 170b. Pressure applied to closure grips 172a and 172b cause cryogenic matter application elements 170a and 170b to close on and substantially encase the skin tag.

It will be appreciated the embodiments illustrated herein may be shown with a vertical valve, the tweezer applicator devices of the present invention may also be adapted to be used with substantially any suitable valve configuration such as, but not limited to, toggle valves or tilt valves.

It will be appreciated that in some embodiments of the present invention the cryogenic matter is applied to the application elements before the application elements contact the target skin lesion. In other embodiments, the cryogenic matter is applied to the application elements after the application elements contact the target skin lesion. In still other embodiments, the application of the cryogenic matter to the application elements and the contact of the application elements with the target skin lesion occur substantially simultaneously.

It will be appreciated that the above descriptions are intended only to serve as examples and that many other embodiments are possible within the spirit and the scope of the present invention.

What is claimed is:

1. A tweezers device for the application of cryogenic matter directly on a skin lesion while protecting the collateral skin tissue from being damaged by the cryogenic matter, the device comprising an applicator body configured with first and second opposing tweezer arms, each tweezer arm including an absorbent application element for absorbing cryogenic matter such that when said opposing tweezer arms are closed said absorbent application elements close upon the skin lesion, and said absorbent application elements are configured to absorb and contain the cryogenic matter and apply the cryogenic matter directly on the skin lesion wherein each of said first and second tweezer arms is configured with a hollow interior region, and wherein first and second canisters containing cryogenic matter are deployed within said hollow interior region of said first and second tweezer arms, respectively, and cryogenic matter released from each said canister is applied to its corresponding said absorbent application element.

2. The tweezers device of claim 1, further including at least one cryogenic matter release actuator configured to release cryogenic matter from said canister.

3. The tweezers device of claim 2, wherein said at least one cryogenic matter release actuator is configured as two cryogenic matter release actuators, one said cryogenic matter release actuator being associated with each of said opposing tweezer arms.

4. The tweezers device of claim 3, wherein each of said cryogenic matter release actuators is configured to interact with said canister deployed within said opposing tweezer arm with which said cryogenic matter release actuator is associated.

5. The tweezers device of claim 3, wherein each of said cryogenic matter release actuators is configured to interact with a displaceable tweezer arm tip deployed within said opposing tweezer arm with which said cryogenic matter release actuator is associated.

6. A method for the application of cryogenic matter directly on a skin lesion while protecting the collateral skin tissue from being damaged by the cryogenic matter, the method comprising:
(a) providing an application device having an applicator body configured with first and second opposing tweezer arms, each tweezer arm including an absorbent application element for absorbing and containing cryogenic matter such that when said opposing tweezer arms are closed said absorbent application elements close upon the skin lesion, wherein each of said first and second tweezer arms is configured with a hollow interior region, and wherein first and second canisters containing cryogenic matter are deployed within said hollow interior region of said first and second tweezer arms, respectively, such that cryogenic matter released from each said canister is applied to its corresponding said absorbent application element;
(b) applying cryogenic matter to each of said absorbent application elements such that each of said absorbent application elements absorbs and contains cryogenic matter;
(c) closing said opposing tweezer arms about the skin lesion, thereby closing said absorbent application elements upon the skin lesion so as to apply cryogenic matter directly on the skin lesion; and
(d) removing said application, device from the skin lesion.

7. The method of claim 6, wherein said applying cryogenic matter to each of said absorbent application elements is accomplished using two cryogenic matter release actuators, one said cryogenic matter release actuator being associated with each of said opposing tweezer arms.

8. The method of claim 7, wherein each of said cryogenic matter release actuators is implemented so as to interact with said canister deployed within said opposing tweezer arm with which said cryogenic matter release actuator is associated.

9. The method of claim 7, wherein each of said cryogenic matter release actuators is implemented so as to interact with a displaceable tweezer arm lip deployed within said opposing tweezer arm with which said cryogenic matter release actuator is associated.

10. The method of claim 6, wherein said steps (b) and (c) occur substantially simultaneously.

11. A device for the application of cryogenic matter directly on a skin lesion, the device comprising
(a) an applicator body having first and second tweezer arms, wherein each of said first and second tweezer arms is configured with it hollow interior region, and wherein first and second canisters containing cryogenic matter are deployed within said hollow interior region of said first and second tweezer arms, respectively:
(b) two cryogenic matter release actuators, one said cryogenic matter release actuator being associated with each of said arms;
(c) an application tip associated with at least one of said arms, said application tip having at least one absorbent application element extending therefrom; and
(d) at least one cryogenic delivery passageway configured in each said arm so as to provide fluid communication between each said canister in each said arm and said absorbent application element;
wherein cryogenic matter released from each said canister is delivered to said absorbent application element such that the cryogenic matter is applied to said absorbent application element and said absorbent application element is configured to absorb and contain the cryogenic matter.

12. The device of claim 11, wherein said application tip is deployed between distal ends of said arms so as to engage both said arms.

* * * * *